US010324582B2

(12) United States Patent
Sekiguchi et al.

(10) Patent No.: US 10,324,582 B2
(45) Date of Patent: Jun. 18, 2019

(54) MEDICAL IMAGE DISPLAY APPARATUS, METHOD FOR CONTROLLING THE SAME

(71) Applicant: CANON KABUSHIKI KAISHA, Tokyo (JP)

(72) Inventors: Hiroyuki Sekiguchi, Kyoto (JP); Gakuto Aoyama, Kyoto (JP); Yutaka Emoto, Kyoto (JP); Koji Sakai, Kyoto (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 522 days.

(21) Appl. No.: 14/736,347

(22) Filed: Jun. 11, 2015

(65) Prior Publication Data

US 2015/0363054 A1  Dec. 17, 2015

(30) Foreign Application Priority Data

Jun. 11, 2014  (JP) .................................. 2014-120842

(51) Int. Cl.
*A61B 6/00* (2006.01)
*A61B 8/00* (2006.01)
(Continued)

(52) U.S. Cl.
CPC .......... *G06F 3/04817* (2013.01); *A61B 6/463* (2013.01); *A61B 8/461* (2013.01);
(Continued)

(58) Field of Classification Search
CPC ............ G06F 3/04842; G06F 3/04845; G06F 3/04886; G06F 19/321; G06F 2203/04806;
(Continued)

(56) References Cited

U.S. PATENT DOCUMENTS 6,785,410 B2   8/2004  Vining et al.
7,058,901 B1*  6/2006  Hafey ................. G06F 19/3406
                                                            345/619
(Continued)

FOREIGN PATENT DOCUMENTS

CN      1719446 A     1/2006
CN    101053521 A    10/2007
(Continued)

OTHER PUBLICATIONS

Office Action issued in Chinese Patent Application No. 201510319870.X dated Sep. 1, 2017. English translation provided.
(Continued)

*Primary Examiner* — Nicholas Ulrich
(74) *Attorney, Agent, or Firm* — Rossi, Kimms & McDowell LLP

(57) ABSTRACT

Aspects of the invention are directed to a medical image display apparatus for displaying a thumbnail image corresponding to medical image data. The medical image data can be displayed in a display area upon selection of the thumbnail image. A display method of the medical image data in the display area can be determined, based on a designated position in the thumbnail image when the thumbnail image is selected by a user. Medical image data is displayed in the display area, according to the determined display method.

34 Claims, 13 Drawing Sheets

(51) Int. Cl.
  *G06F 19/00* (2018.01)
  *G16H 30/20* (2018.01)
  *G16H 30/40* (2018.01)
  *G06F 3/0481* (2013.01)
  *G06F 3/0482* (2013.01)
  *G06F 3/0484* (2013.01)
  *G06F 3/0488* (2013.01)

(52) U.S. Cl.
  CPC ........ *G06F 3/0482* (2013.01); *G06F 3/04883* (2013.01); *G06F 19/321* (2013.01); *G16H 30/20* (2018.01); *G16H 30/40* (2018.01)

(58) Field of Classification Search
  CPC ......... G06F 3/0484; G06F 2203/04803; G06F 19/32; G06F 19/327; G06F 19/34; G06F 19/3487; G06F 19/322; G06F 19/3443; G06F 19/345; G06F 3/04883; G06F 3/04817; H04N 1/00461; H04N 21/4312; H04N 21/4725; H04N 21/4728; H04N 1/00442; H04N 1/00453; A61B 6/463; A61B 1/00045; A61B 6/465; A61B 8/463; A61B 8/461; G06T 2219/028; G16H 30/20; G16H 30/40
  See application file for complete search history.

(56) References Cited

U.S. PATENT DOCUMENTS

| | | | |
|---|---|---|---|
| 7,683,909 B2 | 3/2010 | Takekoshi | |
| 8,312,374 B2* | 11/2012 | Ozawa | G06F 17/30277 345/157 |
| 8,447,090 B2 | 5/2013 | Wakai et al. | |
| 8,634,611 B2 | 1/2014 | Minakuchi et al. | |
| 8,731,263 B2* | 5/2014 | Fukatsu | G06F 19/321 382/128 |
| 8,797,424 B2 | 8/2014 | Oh et al. | |
| 8,913,078 B2* | 12/2014 | Masumoto | G06F 19/321 345/619 |
| 8,971,601 B2 | 3/2015 | Zaiki et al. | |
| 9,019,301 B2 | 4/2015 | Matsue et al. | |
| 9,122,773 B2 | 9/2015 | Li et al. | |
| 9,262,444 B2* | 2/2016 | Gross | G06F 17/30274 |
| 2003/0071829 A1* | 4/2003 | Bodicker | G06F 17/30274 345/619 |
| 2007/0065044 A1* | 3/2007 | Park | G06F 17/30247 382/305 |
| 2007/0242069 A1 | 10/2007 | Matsue et al. | |
| 2008/0294974 A1* | 11/2008 | Nurmi | G06F 17/30905 715/204 |
| 2010/0131890 A1* | 5/2010 | Natanzon | G06F 3/0481 715/808 |
| 2011/0028825 A1 | 2/2011 | Douglas et al. | |
| 2011/0149147 A1* | 6/2011 | Oh | H04N 9/8042 348/441 |
| 2012/0299818 A1 | 11/2012 | Li et al. | |
| 2014/0013280 A1 | 1/2014 | Yoshioka et al. | |
| 2014/0341450 A1* | 11/2014 | Sedan | H04N 19/132 382/128 |

FOREIGN PATENT DOCUMENTS

| | | |
|---|---|---|
| CN | 101398742 A | 4/2009 |
| CN | 101645111 A | 2/2010 |
| CN | 101662584 A | 3/2010 |
| CN | 102596035 A | 7/2012 |
| CN | 102609175 A | 7/2012 |
| CN | 103198499 A | 7/2013 |
| EP | 2533543 A2 | 12/2012 |
| JP | 2005510326 A | 4/2005 |
| JP | 2007029248 A | 2/2007 |
| JP | 2008077210 A | 4/2008 |
| JP | 2009070074 A | 4/2009 |
| JP | 2011130433 A | 6/2011 |
| JP | 2011217947 A | 11/2011 |
| JP | 2012000472 A | 1/2012 |
| JP | 2012081180 A | 4/2012 |
| JP | 2012247879 A | 12/2012 |
| JP | 2012247880 A | 12/2012 |
| JP | 2013152534 A | 8/2013 |
| JP | 2014000475 A | 1/2014 |
| JP | 2014012040 A | 1/2014 |
| JP | 2014012208 A | 1/2014 |
| KR | 1020100071595 A | 6/2010 |
| WO | 2013046940 A1 | 4/2013 |

OTHER PUBLICATIONS

Office Action issued in U.S. Appl. No. 14/736,335 dated Oct. 6, 2017.
Office Action issued in Chinese Appln. No. 201510312174.6 dated Jan. 19, 2018. English translation provided.
Notice of Allowance issued in U.S. Appl. No. 14/736,335 dated Jul. 3, 2018.
Office Action issued in U.S. Appl. No. 14/736,335 dated Apr. 12, 2018.
Office Action issued in Japanese Appln. No. 2014120582 dated May 22, 2018.
Notice of Allowance issued in U.S. Appl. No. 14/736,335 dated Nov. 7, 2018.

\* cited by examiner

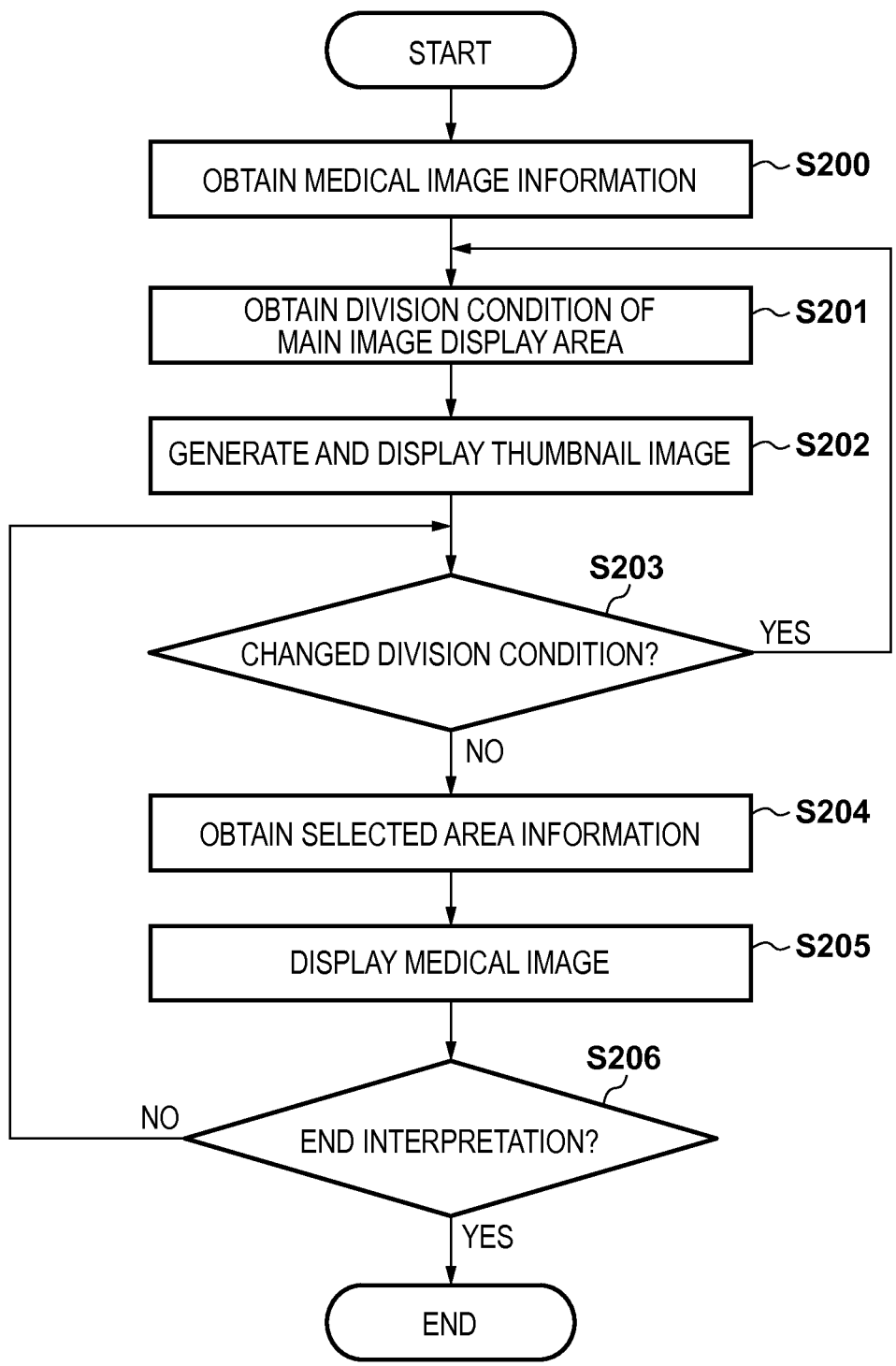

F I G. 14

| IMAGE INFORMATION | | DIVISION CONDITION | |
|---|---|---|---|
| MODALITY | IMAGE CAPTURE SITE | LOCATION OF NON-ASSOCIATED AREA | SHAPE OF NON-ASSOCIATED AREA |
| CT | BREAST REGION | CENTER | CIRCLE |
| CT | ABDOMINAL REGION | UPPER RIGHT, UPPER LEFT | CIRCLE |
| CT | HEAD REGION | LOWER RIGHT | CIRCLE |
| CT | OTHERS | UPPER CENTER | RECTANGLE |
| MRI | HEAD REGION | UPPER RIGHT | CIRCLE |
| MRI | OTHERS | UPPER CENTER | RECTANGLE |
| PET | ALL | UPPER CENTER | CIRCLE |
| CR | LIMBS | UPPER LEFT, LOWER RIGHT | RECTANGLE |
| CR | OTHERS | UPPER CENTER | RECTANGLE |
| OTHERS | ALL | UPPER CENTER | CIRCLE |

F I G. 15

| IMAGE INFORMATION | | DISPLAY CONDITION IN MAIN DISPLAY AREA |
|---|---|---|
| MODALITY | IMAGE CAPTURE SITE | |
| CT | BREAST REGION | MPR DISPLAY |
| CT | ABDOMINAL REGION | MPR DISPLAY |
| CT | HEAD REGION | TIME-COURSE DATA DISPLAY |
| CT | OTHERS | DIFFERENT CONDITION DATA DISPLAY |
| MRI | HEAD REGION | TIME-COURSE DATA DISPLAY |
| MRI | OTHERS | DIFFERENT CONDITION DATA DISPLAY |
| PET | ALL | DIFFERENT CONDITION DATA DISPLAY |
| CR | LIMBS | FULL-SCREEN DISPLAY |
| CR | OTHERS | FULL-SCREEN DISPLAY |
| OTHERS | ALL | DIFFERENT CONDITION DATA DISPLAY |

MEDICAL IMAGE DISPLAY APPARATUS, METHOD FOR CONTROLLING THE SAME

BACKGROUND OF THE INVENTION

Field of the Invention

The present invention relates to a medical image display apparatus, and a method for controlling the same.

Description of the Related Art

In the medical field, medical image capturing apparatuses such as X-ray computed tomography (CT) apparatuses, magnetic resonance imaging (MRI) apparatuses, and positron emission tomography (PET) apparatuses are used to capture medical images. Such captured medical images are subjected to various types of image processing, and stored for a certain period of time in data servers in hospitals. When making diagnoses with images, doctors use a medical image display apparatus (sometimes referred to as a viewer) to search for a target medical image and display it on a monitor, while using various functions of the medical image display apparatus (Japanese Patent Laid-Open No. 2012-000472).

FIG. 16 is a diagram showing an exemplary screen configuration of a commonly used medical image display apparatus. A thumbnail display area 1601 is an area for displaying a thumbnail image of at least one piece of medical image data previously or currently captured from one patient. Numerals 1603 to 1606 denote thumbnail images generated from medical image data. A main display area 1602 is an area for displaying medical image data on which interpretation is to be performed by a user. When medical image data is displayed in the main display area 1602, the displayed medical image data can be subjected to various functions of the medical image display apparatus.

The main display area 1602 can be divided into a plurality of areas, and different images can be simultaneously displayed respectively in the plurality of partial display areas (hereinafter, referred to as partial areas 1608 to 1611) obtained by the division. In FIG. 16, the main display area 1602 is divided into four areas consisting of the partial areas 1608 to 1611. Medical image data on which interpretation is to be performed or to which reference is to be made may be displayed in a freely selected partial area, and interpretation is performed by the user. In the user interface in FIG. 16, a freely selected thumbnail image (e.g., the thumbnail image 1603) is dragged and dropped by the user into a freely selected partial area (e.g., the partial area 1609) of the main display area 1602. Accordingly, medical image data corresponding to the thumbnail image 1603 is displayed in the partial area 1609.

However, with the above-described technique, in order to display a desired thumbnail image in a desired partial area of the main display area 1602, it is necessary to drag and drop the thumbnail image into the partial area. For example, the procedure is required that moves a mouse cursor onto the thumbnail image 1603 and selects the thumbnail image, further moves the mouse cursor onto the partial area 1609 of the main display area 1602, and releases the mouse cursor. Accordingly, there is a problem that it requires effort to designate medical image data that is to be displayed and a display position.

In consideration of such a problem, a method has been proposed in which, when any thumbnail image is selected by a user, the system automatically determines a position where medical image data corresponding to the thumbnail image is to be displayed in the main display area 1602. For example, a method has been proposed in which, when the thumbnail image is selected, a partial area not displaying medical image data is automatically identified, and medical image data corresponding to the selected thumbnail image is displayed in the identified partial area. Also, a method has been proposed in which the order for using the partial areas of the main display area is determined in advance, and medical image data is displayed according to that order. However, all of these methods employ a technique for displaying medical image data in a partial area determined by the system, and, thus, there is a problem that data cannot be always displayed in a partial area intended by the user.

SUMMARY OF THE INVENTION

An embodiment of the present invention provides a medical image display apparatus that can display freely selected medical image data as intended by a user with a small amount of effort, a method for controlling the same, and a program.

According to one aspect of the present invention, there is provided a medical image display apparatus for displaying a thumbnail image corresponding to medical image data, and displaying the medical image data in a display area upon selection of the thumbnail image, comprising: a determination unit configured to determine a display method of the medical image data in the display area, based on a designated position in the thumbnail image when the thumbnail image is selected by a user; and a display control unit configured to display the medical image data in the display area, according to the display method determined by the determination unit.

According to another aspect of the present invention, there is provided a medical image display apparatus for displaying a thumbnail image corresponding to medical image data, and displaying the medical image data in a display area upon selection of the thumbnail image, comprising: an acceptance unit configured to accept an instruction to select the thumbnail image and input of directional information from a user; a determination unit configured to determine a display method of the medical image data in the display area, based on the directional information; and a display control unit configured to display the medical image data in the display area, according to the display method determined by the determination unit.

According to another aspect of the present invention, there is provided a method for controlling a medical image display apparatus for displaying a thumbnail image corresponding to medical image data, and displaying the medical image data in a display area upon selection of the thumbnail image, comprising: a determination step of determining a display method of the medical image data in the display area, based on a designated position in the thumbnail image when the thumbnail image is selected by a user; and a display control step of displaying the medical image data in the display area, according to the display method determined in the determination step.

According to another aspect of the present invention, there is provided a method for controlling a medical image display apparatus for displaying a thumbnail image corresponding to medical image data, and displaying the medical image data in a display area upon selection of the thumbnail image, comprising: an acceptance step of accepting an instruction to select the thumbnail image and input of directional information from a user; a determination step of determining a display method of the medical image data in the display area, based on the directional information; and a display control step of displaying the medical image data in the display area, according to the display method determined in the determination step.

Further features of the present invention will become apparent from the following description of exemplary embodiments with reference to the attached drawings.

BRIEF DESCRIPTION OF THE DRAWINGS

FIG. 2 is a flowchart illustrating the overall processing of the first embodiment.

FIG. 14 is a table showing a correspondence example between the image information and the division condition.

FIG. 15 is a table showing a correspondence example between the image information and the display condition in the main display area.

DESCRIPTION OF THE EMBODIMENTS

Hereinafter, some preferred embodiments of the present invention will be described with reference to the appended drawings. Note that the scope of the invention is not limited to these examples.

First Embodiment

Figure 1:
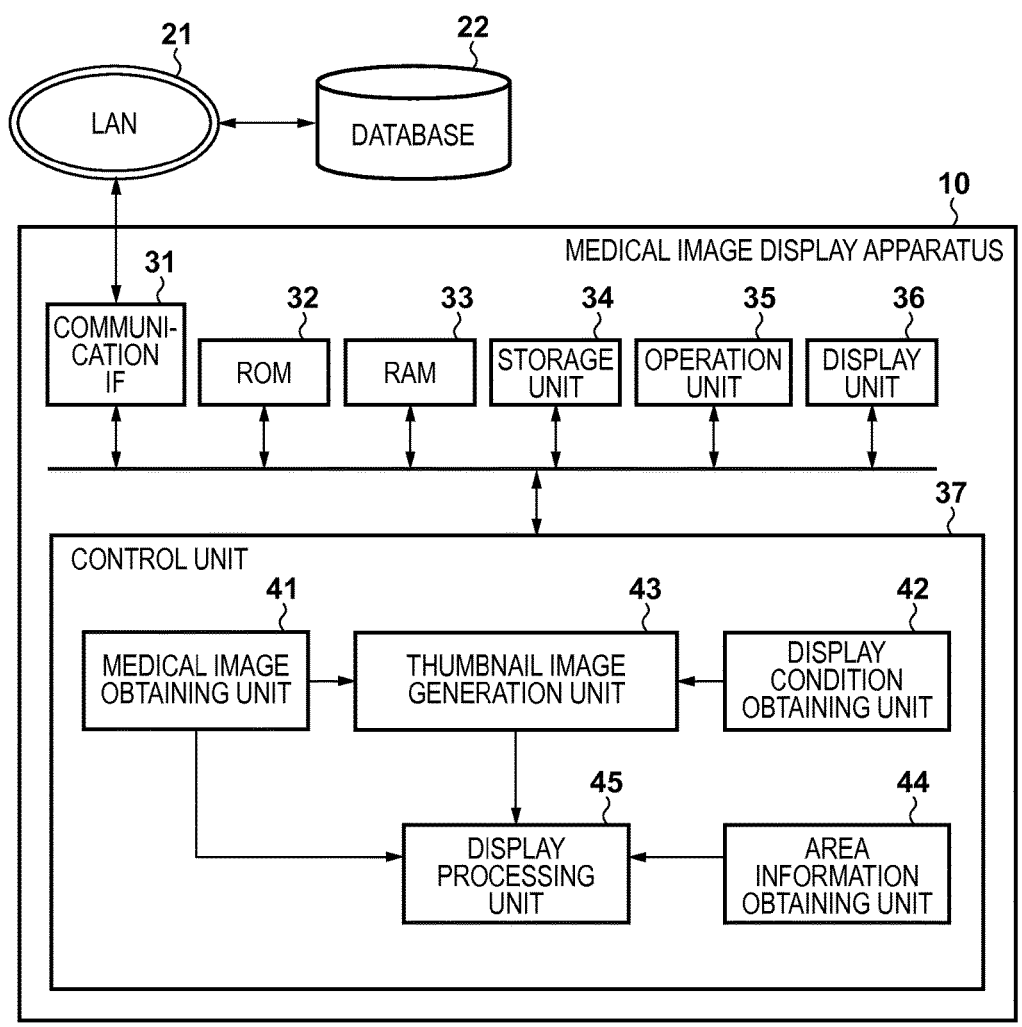
FIG. 1 is a block diagram showing a configuration example of a medical image display apparatus according to a first embodiment.

FIG. 1 is a diagram showing the overall configuration of a medical image display system including a medical image display apparatus according to the first embodiment. The medical image display system includes a medical image display apparatus 10 and a database 22, and these apparatuses are communicably connected to each other via an LAN 21, which is an exemplary communication means. The database 22 can manage and store examination information such as medical image data. The medical image display apparatus 10 obtains medical image data managed in the database 22, via the LAN 21. The medical image display apparatus 10 displays a thumbnail image corresponding to medical image data, and displays the medical image data in a display area upon selection of the thumbnail image.

The medical image display apparatus 10 has a functional configuration including a communication interface (communication IF) 31, a ROM 32, a RAM 33, a storage unit 34, an operation unit 35, a display unit 36, and a control unit 37. The communication IF 31 is realized by a LAN card or the like, and is used for communication between an external apparatus (e.g., the database 22) and the medical image display apparatus 10 via the LAN 21. The read only memory (ROM) 32 is realized by a non-volatile memory or the like, and stores various programs and the like. The random access memory (RAM) 33 is realized by a volatile memory or the like, and temporarily stores various types of information used by the control unit 37 or the like. The storage unit 34 is realized by a hard disk drive (HDD) or the like, and stores various types of information. The operation unit 35 is realized by a keyboard, a mouse, or the like, and is used to input instructions from a user to the apparatus. The display unit 36 is realized by a display screen or the like, and displays various types of information.

The control unit 37 is realized by a central processing unit (CPU) or the like, and performs comprehensive control of the processing in the medical image display apparatus 10. The control unit 37 has a functional unit configuration including a medical image obtaining unit 41, a display condition obtaining unit 42, a thumbnail image generation unit 43, an area information obtaining unit 44, and a display processing unit 45. Note that at least part of the functional units included in the control unit 37 may be realized by an independent apparatus, and each unit may be realized by software for realizing the function. In this embodiment, it is assumed that each functional unit is realized by software.

The medical image obtaining unit 41 obtains medical image data via the communication IF 31 and the LAN 21 from the database 22, and outputs it to the thumbnail image generation unit 43 and the display processing unit 45. The display condition obtaining unit 42 obtains a division condition of a main display area (e.g., a main display area 102 in FIG. 3A) displayed on the display unit 36, and outputs it to the thumbnail image generation unit 43. The division condition indicates a manner for dividing the main display area into a plurality of partial areas. The thumbnail image generation unit 43 generates a thumbnail image, using the medical image data obtained by the medical image obtaining unit 41 and the division condition of the main display area obtained by the display condition obtaining unit 42. The area information obtaining unit 44 obtains selected area information indicating an area selected by the user via the operation unit 35, in the thumbnail image displayed on the display unit 36, and outputs it to the display processing unit 45. The display processing unit 45 displays the thumbnail image generated by the thumbnail image generation unit 43, on the display unit 36. Furthermore, the display processing unit 45 displays the medical image data obtained from the medical image obtaining unit 41, in the main display area of the display unit 36, according to the selected area information obtained by the area information obtaining unit 44.

Figure 3A:
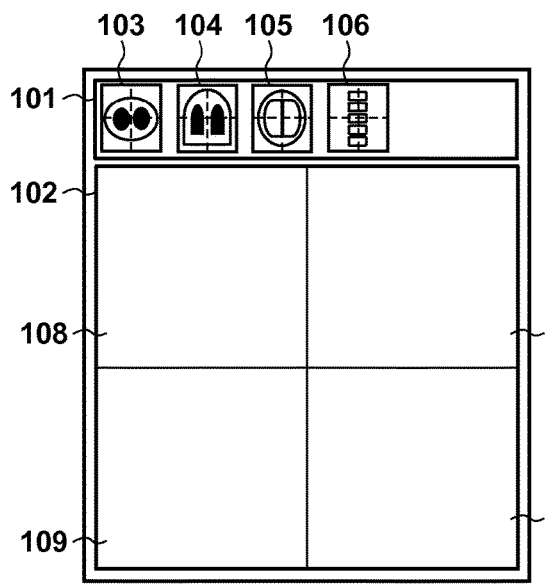
FIGS. 3A and 3B are diagrams illustrating a configuration example of a display screen according to the first embodiment.
Figure 3B:
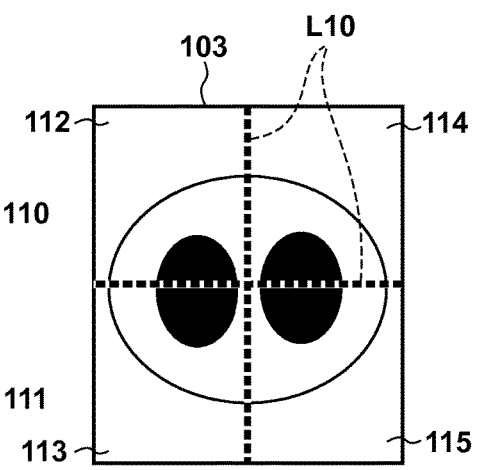
Figure 4A:
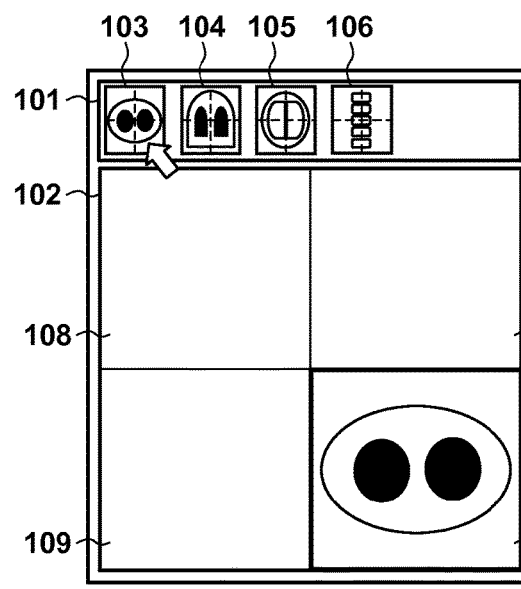
FIGS. 4A and 4B are diagrams illustrating a designated position on a thumbnail image and a display position of medical image data.
Figure 4B:
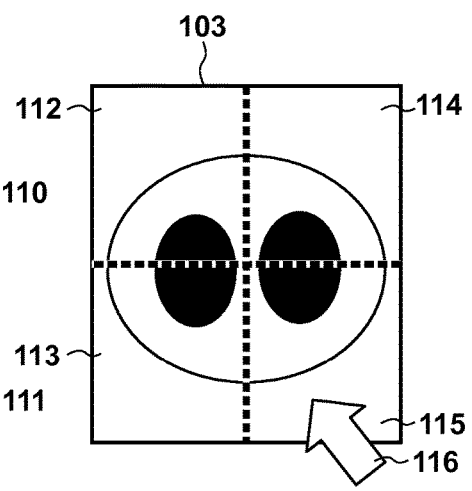

Next, the overall processing by the control unit 37 in this embodiment will be described with reference to FIGS. 2, 3A, 3B, 4A, and 4B. FIG. 2 is a flowchart of the processing performed by the control unit 37. FIGS. 3A and 4A show exemplary screens displayed on the display unit 36 through the processing (described later). FIGS. 3B and 4B are diagrams showing, in more detail, a thumbnail image 103 shown in FIGS. 3A and 4A. As shown in FIGS. 3A and 4A, the screen displayed on the display unit 36 by the display processing unit 45 includes a thumbnail display area 101 and a main display area 102. The thumbnail display area 101 displays a thumbnail image of medical image data. In the example in FIG. 3A, thumbnail images 103 to 106 are displayed. The main display area 102 displays medical image data, wherein medical image data can be displayed in each of a plurality of partial areas (partial areas 108 to 111 in the example in the diagrams) obtained by dividing the display area.

In this embodiment, the area information obtaining unit 44 obtains a designated position in a thumbnail image when the thumbnail image is selected by a user, and the display processing unit 45 determines a display method of the medical image data in the main display area 102, based on the obtained designated position. The display processing unit 45 performs display control so as to display the medical image data in the main display area 102 according to the determined display method. Accordingly, for example, if the user's designated position (designated position indicated by an arrow 116) is in the lower right in the thumbnail image 103 as shown in FIG. 4B, the medical image data corresponding to the thumbnail image 103 is displayed in the partial area 111 in the lower right in the main display area 102. Hereinafter, this processing will be described in more detail.

In step S200 in FIG. 2, the medical image obtaining unit 41 reads medical image data via the communication IF 31 and the LAN 21 from the database 22. In step S201, the display condition obtaining unit 42 obtains a division condition indicating a manner for dividing the main display area displayed on the display unit 36 into the partial areas. For example, if the number of areas obtained by the division in the main display area is taken as l, the number of rows is taken as n, and the number of columns is taken as m, (l, n, m)=(4, 2, 2) is obtained as a division condition in the case of the display state in FIG. 3A. Note that how to indicate the division condition is not limited to this.

In step S202, the thumbnail image generation unit 43 generates a thumbnail image corresponding to the medical image data read in step S200, through the following processing. First, the thumbnail image generation unit 43 generates image data (hereinafter, referred to as corresponding image data) corresponding to the medical image data read in step S200. For example, if the read medical image data is two-dimensional medical image data (one slice image), the corresponding image data is an image obtained by changing (e.g., reducing) the size of that slice image, or an image obtained by extracting part of the slice image. On the other hand, if the read medical image data is three-dimensional medical image data (a plurality of slice images), the corresponding image data is an image obtained by changing (e.g., reducing) the size of a slice image representative of the three-dimensional medical image data, or an image obtained by changing the size of a slice image at a predetermined position (e.g., first slice image). Alternatively, the corresponding image data may be an image obtained by extracting part of the slice image.

Next, the thumbnail image generation unit 43 divides the corresponding image data into a plurality of divided areas, based on the division condition obtained in step S201. For example, if (l, n, m)=(4, 2, 2) is obtained in step S201, the corresponding image data is divided in a similar manner according to the condition (l, n, m)=(4, 2, 2). Accordingly, for example, divided areas 112 to 115 as shown in FIG. 3B are obtained according to the division condition of the main display area 102 as in FIG. 3A. Subsequently, the thumbnail image generation unit 43 generates boundary lines (boundary lines L10 in FIG. 3B) such that the divided areas can be seen, and displays the generated boundary lines such that they are overlaid on the corresponding image data, thereby generating a thumbnail image on which the boundary lines are drawn. The thumbnail image generation unit 43 performs this processing on all of the medical image data read in step S200. The display processing unit 45 displays the thumbnail images (the thumbnail images 103 to 106 in FIG. 3A) generated by the thumbnail image generation unit 43 such that the images are arranged side by side in the thumbnail display area 101. If the division condition of the main display area 102 is approximately 2×2 as shown in FIGS. 3A and 4A, the operability is not lowered even without displaying the boundary lines, as long as the arrangement of the partial areas and the arrangement of the divided areas are in conformity with each other. In this case, the corresponding image data is used as it is as a thumbnail image. In any case, the control unit 37 manages association between the partial areas and the divided areas.

In step S203, the control unit 37 obtains a division condition of the main display area 102, and judges whether or not the division condition has been changed. Note that the division condition of the main display area 102 can be changed according to an instruction from the user received via the operation unit 35. The method for changing the division condition may be realized using a known technique in the field of commonly used medical image viewers. In step S203, if it is judged that the division condition has not been changed, the procedure advances to step S204, and, if it is judged that the division condition has been changed, the procedure returns to step S201.

In step S204, the area information obtaining unit 44 obtains information indicating a divided area in the thumbnail image selected by the user using the operation unit 35. For example, if the user clicks on the divided area 115 in the thumbnail image 103 using a mouse, the area information obtaining unit 44 obtains information indicating the divided area 115. FIGS. 4A and 4B show a screen example on the display unit 36 at the time of this operation. The arrow 116 indicates, for example, a designated position (e.g., a mouse pointer, etc.) of input performed with the operation unit 35. In FIG. 4B, the divided area 115 is the divided area including the designated position.

In step S205, the display processing unit 45 displays the medical image data corresponding to the thumbnail image selected in step S204, in the partial area in the main display area 102 associated with the designated divided area. In the above-described example, the divided area 115 in the thumbnail image 103 is selected, and, thus, the medical image data corresponding to the thumbnail image 103 is displayed in the partial area 111 in the main display area 102 as shown in FIG. 4A. If another piece of medical image data has been already displayed in the partial area 111, the already displayed medical image data is deleted from the partial area 111, after which the medical image data corresponding to the thumbnail image 103 is displayed.

In step S206, the control unit 37 judges whether or not an instruction to end the interpretation has been received from the user via the operation unit 35. The instruction to end the interpretation is given, for example, by the user clicking on an unshown interpretation end button. If an instruction to end the interpretation has been received, the procedure in FIG. 2 is ended. If an instruction to end the interpretation has not been received, the procedure returns to step S203.

As described above, with the medical image display apparatus according to the first embodiment, a plurality of partial areas obtained by dividing the main display area and a plurality of divided areas obtained by dividing the thumbnail image are associated with each other. For example, as in FIG. 3A showing the plurality of partial areas 108 to 111 and the plurality of divided areas 112 to 115, the thumbnail image is divided such that the relative positional relationship therebetween is maintained. When the thumbnail image is selected by the user, a display method is determined such that the medical image data corresponding to the selected thumbnail image is displayed in a partial area in the main display area associated with a divided area to which the designated position belongs. With this configuration, the following effects are obtained. That is to say, if any divided area in any thumbnail image is selected, medical image data corresponding to the thumbnail image can be displayed in a partial area in the main display area associated with the selected divided area. Accordingly, it is possible to provide a medical image display apparatus and a medical image display method that require less user effort, because effort-requiring operations such as conventional drag-and-drop operation do not have to be performed at the time of interpretation.

MODIFIED EXAMPLE 1-1

Figure 5A:
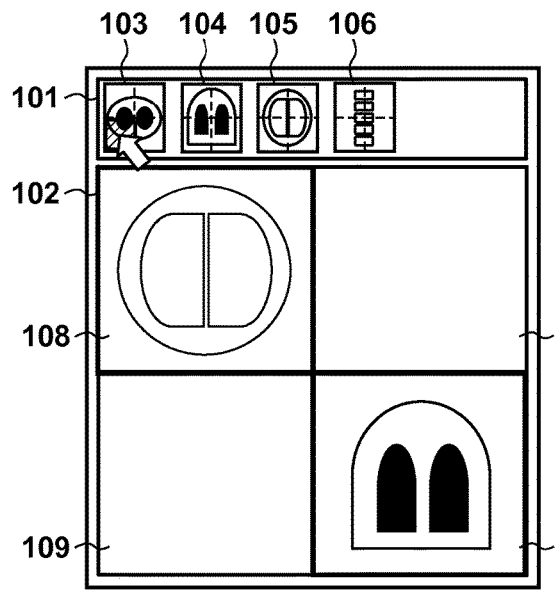
FIGS. 5A and 5B are diagrams illustrating an emphasis display method of a divided area in a thumbnail image.
Figure 5B:
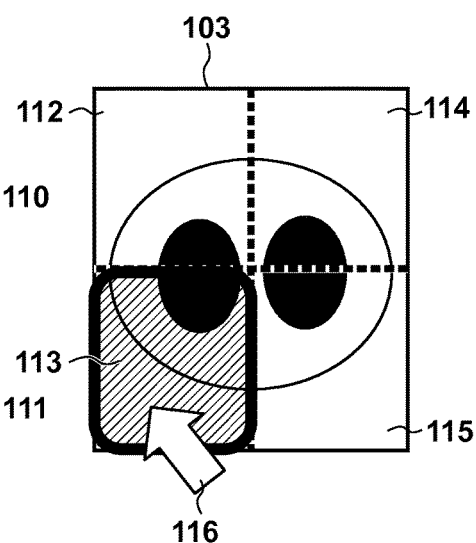

In the first embodiment described above, the user selects a divided area in the thumbnail image via the operation unit 35 in step S204. At that time, the divided area including the currently designated position designated with the operation unit 35 may be displayed in an emphasized manner such that the selected divided area can be more easily seen. Note that the boundary lines L10 may be displayed or may not be displayed. FIG. 5A shows a screen example on the display unit 36, in which a divided area in the thumbnail image is displayed in an emphasized manner. FIG. 5B is a diagram showing, in more detail, the thumbnail image 103 in FIG. 5A. In the example in FIGS. 5A and 5B, the currently designated position indicated by the arrow 116 is positioned on the divided area 113 in the thumbnail image 103, and the divided area 113 is displayed in an emphasized manner by overlaying a marker thereon.

The marker may have any form (color, shape, size, etc.) as long as the user can distinguish the divided area from the other divided areas. When the user moves the arrow 116 onto another divided area, the divided area after the movement is displayed in an emphasized manner. For example, when the arrow 116 is moved onto the divided area 115, the marker displaying the divided area 113 in an emphasized manner is deleted, and a marker is overlaid on the divided area 115. Although emphasis display performed by overlaying a marker was described as an example, the emphasis display method may be any method as long as the user can identify the area displayed in an emphasized manner.

With the configuration according to Modified Example 1-1 described above, a display form is changed such that a divided area to which the designated position in the thumbnail image belongs before an instruction to select the thumbnail image is given is identifiable with respect to the other divided areas. Accordingly, before the thumbnail image is selected, the user can more clearly see the currently designated position indicated by the arrow 116, and can more easily see a partial area in which the corresponding medical image is to be displayed.

MODIFIED EXAMPLE 1-2

Figure 6A:
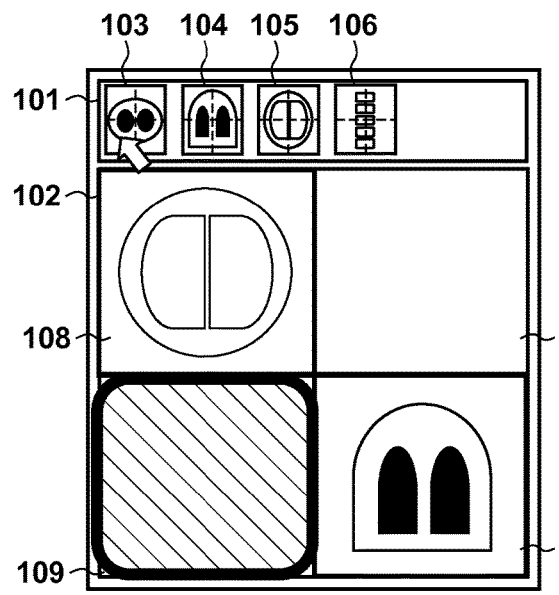
FIGS. 6A and 6B are diagrams illustrating an emphasis display method of a partial area in a main display area.
Figure 6B:
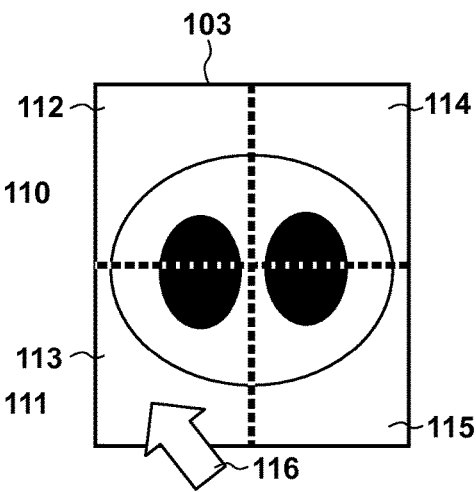

In Modified Example 1-1 in this embodiment, the divided area in the thumbnail image designated with the current position of input performed with the operation unit 35 is displayed in an emphasized manner. However, instead of or in addition to the divided area emphasis display, the associated partial area in the main display area may be displayed in an emphasized manner. FIG. 6A shows a screen example on the display unit 36, in which the partial area in the main display area is displayed in an emphasized manner. FIG. 6B is a diagram showing, in more detail, the thumbnail image 103 in FIG. 6A. The currently designated position indicated by the arrow 116 is positioned on the divided area 113 in the thumbnail image 103, and the partial area 109 in the main display area associated with the divided area 113 is displayed in an emphasized manner by overlaying a marker thereon. When the user moves the arrow 116 onto another divided area on the thumbnail image 103, the partial area in the main display area 102 associated with the divided area after the movement is displayed in an emphasized manner. For example, when the arrow 116 is moved onto the divided area 115, the control unit 37 deletes the marker displaying the partial area 109 in an emphasized manner, and arranges a marker such that it is overlaid on the partial area 111. Although emphasis display performed by overlaying a marker was described as an example, the emphasis display method may be any method as long as the user can identify the area displayed in an emphasized manner.

According to Modified Example 1-2 described above, a display form is changed such that a partial area in the main display area associated with a divided area to which the designated position in the thumbnail image belongs before an instruction to select the thumbnail image is given is identifiable with respect to the other partial areas. For example, when the arrow 116 is moved onto the divided area 113 in the thumbnail image 103, a display form of the partial area 109 in the main display area 102 associated with the divided area 113 is changed as shown in the drawings such that the user can distinguish the partial area from the other partial areas. Accordingly, the user can more easily see a partial area in which the medical image data is to be displayed when an instruction to select the thumbnail image is given at the currently designated position indicated by the arrow 116.

MODIFIED EXAMPLE 1-3

In Modified Examples 1-1 and 1-2 described above, a divided area in the thumbnail image 103 or a partial area in the main display area 102 is displayed in an emphasized manner regardless of the display state of the medical image data in the main display area. In Modified Example 1-3, the emphasis display method is changed according to the display state of the medical image data in the main display area 102. Hereinafter, a description will be given using the main display area 102 in FIG. 5A as an example. If the arrow 116 is positioned on the divided area 112 or 115 in the thumbnail image 103 (a divided area in the thumbnail image associated with a partial area in the main display area 102 in which medical image data has been already displayed), that divided area is displayed in an emphasized manner in red. Meanwhile, if the arrow 116 is positioned on the divided area 113 or 114 in the thumbnail image 103 (a divided area in the thumbnail image associated with the partial area 109 or 110 in the main display area 102 in which no medical image data is displayed), that divided area is displayed in an emphasized manner in blue.

In this manner, according to Modified Example 1-3, a manner in which the display of the divided area to which the designated position belongs is changed (e.g., emphasis method involving the marker color or the frame thickness) varies according to whether or not medical image data has been already displayed in the partial area in the main display area 102. Accordingly, for example, when selecting the thumbnail image, a partial area not displaying medical image data can be more easily designated.

MODIFIED EXAMPLE 1-4

Figure 7A:
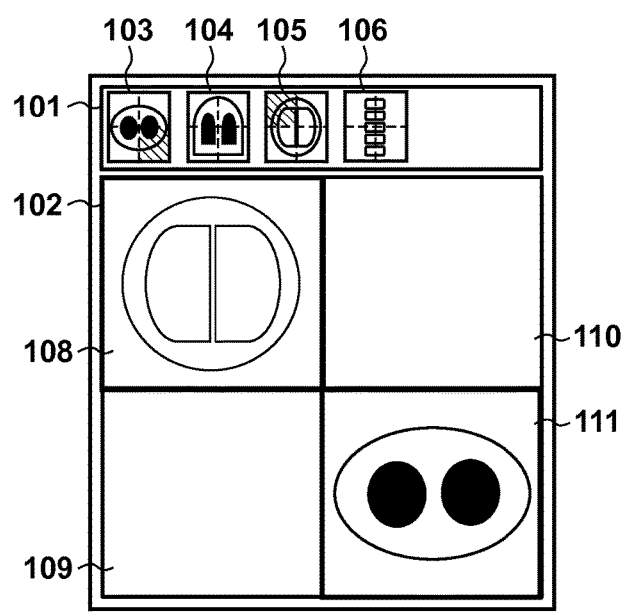
FIGS. 7A to 7C are diagrams illustrating an emphasis display method of a divided area in a thumbnail image.
Figure 7B:
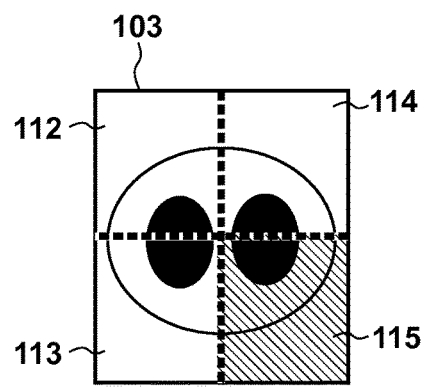
Figure 7C:
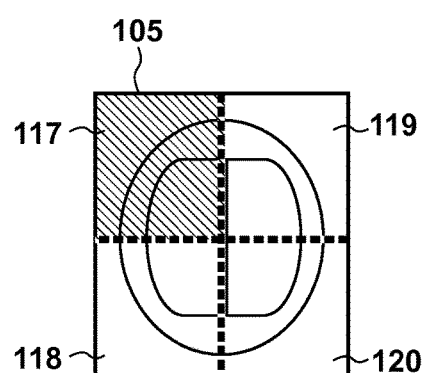

In Modified Example 1-4, according to the display state of medical image data in the main display area, a divided area associated with the partial area displaying the medical image data, of the thumbnail image corresponding to the displayed medical image data, is displayed in an emphasized manner. FIG. 7A shows a screen example on the display unit 36. FIG. 7B is a diagram showing, in more detail, the thumbnail image 103 in FIG. 7A. FIG. 7C is a diagram showing, in more detail, the thumbnail image 105 in FIG. 7A. In FIG. 7A, medical image data corresponding to the thumbnail images 103 and 105 is displayed respectively in the partial areas 108 and 111 in the main display area 102. The medical image data corresponding to the thumbnail image 103 is displayed in the partial area 111, and, thus, the divided area 115 in the thumbnail image 103 is displayed in an emphasized manner by overlaying a marker thereon. This emphasis display indicates a relative position of the partial area 111 in the main display area 102. Furthermore, the medical image data corresponding to the thumbnail image 105 is displayed in the partial area 108 in the main display area 102, and, thus, a divided area 117 in the thumbnail image 105 is displayed in an emphasized manner by overlaying a marker thereon. It is preferable that, if the display state in the main display area 102 is changed in response to the input from the user, the divided area emphasized in each thumbnail image accordingly changes.

As described above, according to Modified Example 1-4, for example, a display form of the divided area 117 associated with the partial area 108, of the thumbnail image 105 corresponding to the medical image data displayed in the partial area 108 in the main display area 102 changes so as to be identifiable with respect to the other divided areas. Accordingly, the user can easily see a thumbnail image whose corresponding medical image data has been already displayed, together with the partial area in which the medical image data is displayed.

MODIFIED EXAMPLE 1-5

In this embodiment, in step S205, if another piece of medical image data (hereinafter, referred to as already displayed image data) has been already displayed in a partial area in the main display area associated with the divided area in the thumbnail image selected in step S204, the already displayed image data is deleted from the partial area. That is, medical image data (hereinafter, referred to as selected image data) indicated by the thumbnail image selected later is preferentially displayed (hereinafter, referred to as overwriting display processing). However, image processing may be performed using the already displayed image data and the selected image data to newly generate image data (hereinafter, referred to as new image data) and the new image data may be displayed (hereinafter, referred to as new image generation processing). For example, as the new image generation processing, known subtraction processing is performed on the already displayed image data and the selected image data, so that difference image data between the already displayed image data and the selected image data is generated and displayed as new image data. Alternatively, as the new image generation processing, known alignment processing and overlapping processing are performed on the already displayed image data and the selected image data, so that image data obtained by overlapping the two pieces of medical image data is generated and displayed as new image data.

In this case, whether to perform the overwriting display processing or to perform the new image generation processing may be easily switched by the user. For example, it may be switched according to the selecting method (user operation form) when selecting a divided area in the thumbnail image in step S204. For example, if the operation unit 35 for giving an instruction to select a divided area is a mouse, the overwriting display processing is performed when a right click operation is performed, and the new image generation processing is performed when a left click operation is performed. Note that Modified Examples 1-1 to 1-5 are applicable also to the second and subsequent embodiments.

Second Embodiment

In the first embodiment, each partial area in the main display area and each divided area in the thumbnail image are associated with each other such that the division state of the main display area and the division state of the thumbnail image are in a similar relationship. In the second embodiment, divided areas in the thumbnail image includes divided areas respectively associated with the partial areas in the main display area (hereinafter, referred to as associated areas), and a divided area associated with none of the partial areas in the main display area (hereinafter, referred to as a non-associated area). If an associated area is designated when selecting the thumbnail image, a first display method is performed in which the medical image data is displayed in a partial area associated with the divided area as in the first embodiment. On the other hand, if a non-associated area is designated when selecting the thumbnail image, the medical image data is displayed according to a second display method (described later in detail with reference to FIGS. 9A to 9D), which is different from the first display method.

FIGS. 8A to 8D show exemplary division conditions of the thumbnail image according to the second embodiment. Hereinafter, a description will be given using, as an example, the state in which the main display area is divided into four areas as shown in FIG. 3A. FIGS. 8A to 8D show examples in which a thumbnail image 801 is divided into associated areas (divided areas 121 to 124) and a non-associated area (a divided area 125). Note that the configuration of the medical image display apparatus 10 according to the second embodiment is as in the first embodiment (FIG. 1). Furthermore, it is assumed that, as in the first embodiment, each functional unit of the control unit 37 is realized by software. Hereinafter, the overall processing in the second embodiment will be described with reference to the flowchart in FIG. 2.

The processes in steps S200 and S201 are similar to those in the first embodiment. In step S202, the thumbnail image generation unit 43 generates a thumbnail image. First, the thumbnail image generation unit 43 generates image data corresponding to the medical image data read in step S200. Next, the generated corresponding image data is divided so as to generate both of an associated area and a non-associated area, using the division condition obtained in step S201. For example, the thumbnail image is divided into areas as shown in the example in FIGS. 8A to 8D.

Figure 8A:
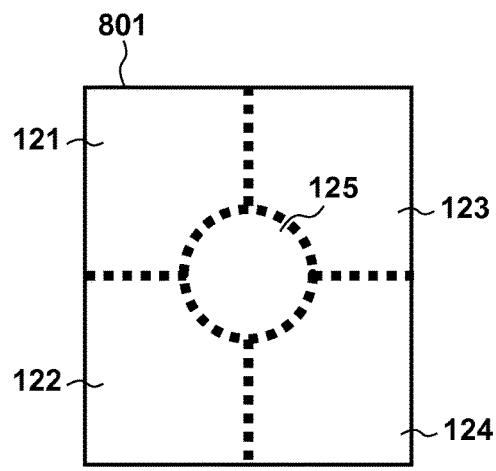
FIGS. 8A to 8D are diagrams showing division examples of a thumbnail image including a non-associated area.
Figure 8B:
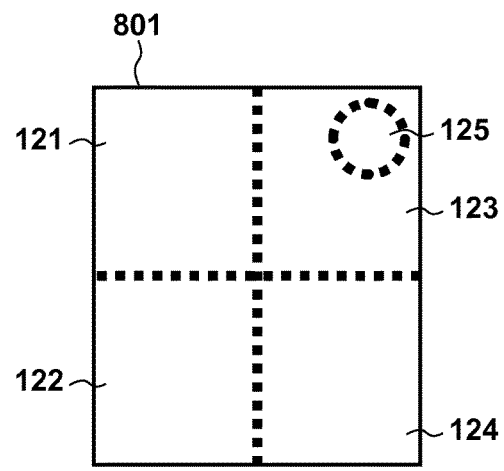
Figure 8C:
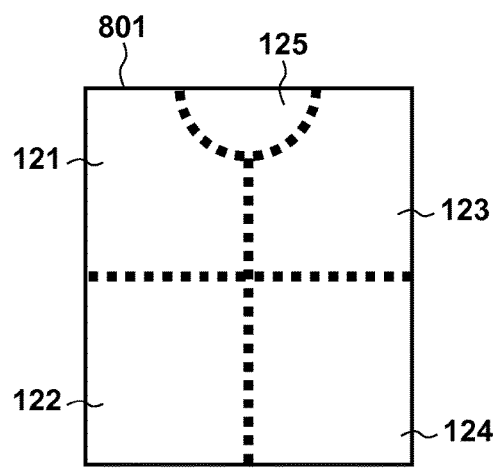
Figure 8D:
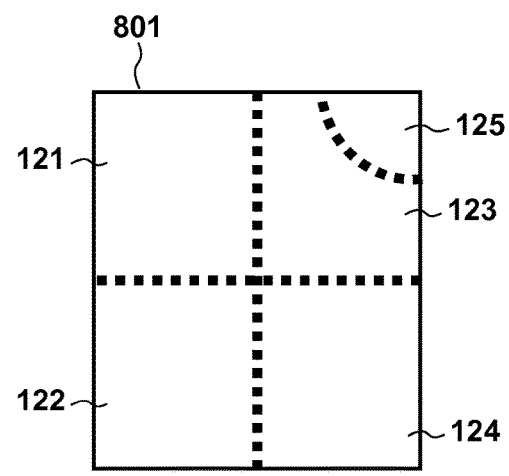

FIG. 8A shows an example in which the divided area 125, which is a non-associated area, is generated at an area centered about the intersection between boundary lines (the boundary lines L10 in FIG. 3B) generated when dividing the thumbnail image 801 into associated areas (the divided areas 121 to 124). FIG. 8B shows an example in which the divided area 125, which is a non-associated area, is generated as an isolated area at a corner of the thumbnail image 801. FIG. 8C shows an example in which the divided area 125, which is a non-associated area, is generated at an area in the shape of a semicircle centered about the intersection between a boundary line generated when dividing the thumbnail image 801 into associated areas (the divided areas 121 to 124) and a frame line of the thumbnail image 801. FIG. 8D shows an example in which the divided area 125, which is a non-associated area, is generated at an area in the shape of a quadrant centered about a corner defined by frame lines of the thumbnail image 801.

Next, the thumbnail image generation unit 43 generates boundary lines such that the divided areas can be seen, and overlays them on the corresponding image data, thereby generating the thumbnail image 801. This processing is performed on all of the medical image data read in step S200, and the generated thumbnail images are displayed side by side in the thumbnail display area. Note that the cases shown in FIGS. 8A to 8D are merely examples, and there is no limitation to these examples as long as the division is performed such that all areas are separated from each other and an associated area and a non-associated area can be easily recognized. The processes in steps S203 and S204 are similar to those in the first embodiment. Note that the boundary lines may not be drawn.

In step S205, the display processing unit 45 displays the medical image data corresponding to the thumbnail image selected in step S204, in the corresponding partial area in the main display area according to the selected divided area. If the selected divided area is an associated area, the processing as in the first embodiment (first display method) is performed. On the other hand, if the selected divided area in the thumbnail image is a non-associated area, the second display method different from the first display method, such as display not depending on the division condition or the display state of the main display area, is performed.

Figure 9A:
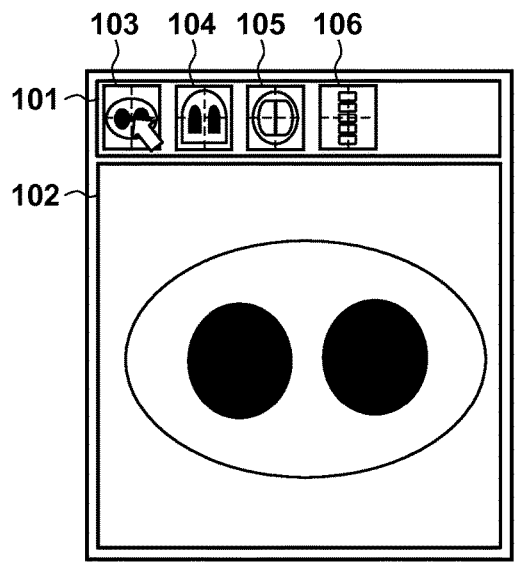
FIGS. 9A to 9D show display examples on the main display area when a non-associated area is selected.
Figure 9B:
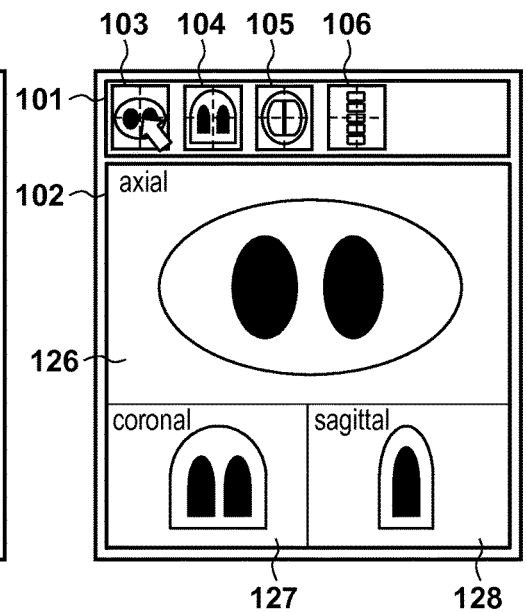

FIGS. 9A to 9D are display screen examples on the display unit 36 realized by the second display method when a non-associated area in the thumbnail image 103 is selected in step S204. FIG. 9A shows an example in which the medical image data corresponding to the thumbnail image 103 is displayed as one screen in the entire main display area 102 (hereinafter, referred to as full-screen display). FIG. 9B shows an example in which the main display area 102 is divided into partial areas 126 to 128, wherein tomographic images obtained by reconstructing the medical image data corresponding to the thumbnail image 103 in tomographic directions according to the multi-planar reconstruction (MPR) are displayed in the respective partial areas (hereinafter, referred to as MPR display). More specifically, the partial area 126 displays a tomographic image (axial image) reconstructed in a body axis direction parallel to the upper-lower (cranio-caudal) direction of the body. The partial area 127 displays a tomographic image (coronal image) reconstructed in a coronal direction parallel to the front-rear (ventrodorsal) direction of the body. The partial area 128 displays a tomographic image (sagittal image) reconstructed in a sagittal direction parallel to the left-right direction of the body.

Figure 9C:
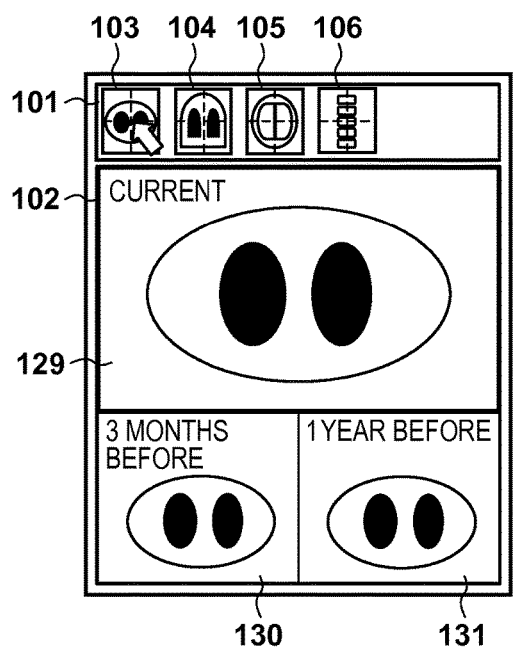
Figure 9D:
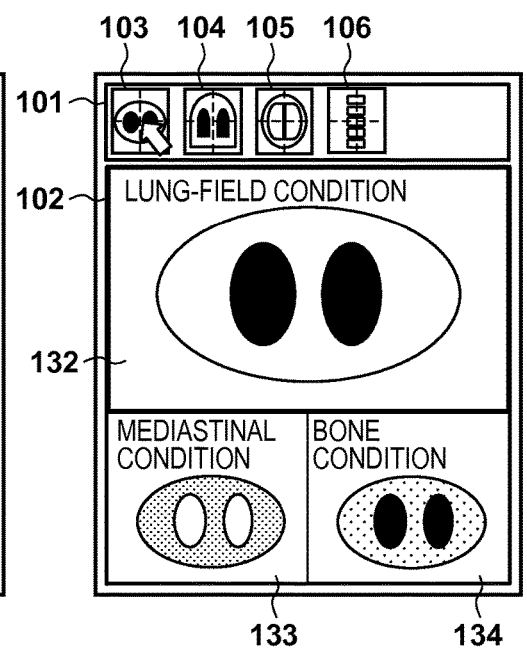

FIG. 9C shows an example in which the main display area 102 is divided into partial areas 129 to 131, wherein medical image data captured from the same patient at different dates and times is displayed in the respective partial areas (hereinafter, referred to as time-course data display). For example, the partial area 129 displays the medical image data corresponding to the thumbnail image 103. The partial area 130 displays medical image data captured from the same patient three months before the thumbnail image 103 was captured. The partial area 131 displays medical image data captured from the same patient one year before the thumbnail image 103 was captured. FIG. 9D shows an example in which the main display area 102 is divided into partial areas 132 to 134, wherein medical image data reconstructed in different reconstruction conditions is displayed in the respective partial areas (hereinafter, referred to as different condition data display). More specifically, the partial area 132 displays medical image data reconstructed in lung-field conditions, of the medical image data corresponding to the thumbnail image 103. The partial area 133 displays medical image data reconstructed in mediastinal conditions, of the medical image data corresponding to the thumbnail image 103. The partial area 134 displays medical image data reconstructed in bone conditions, of the medical image data corresponding to the thumbnail image 103. The display conditions in the main display area when a non-associated area is selected are set in advance.

In the above-described examples, the division state of the main display area is changed when a non-associated area is selected, but the division condition of the thumbnail image may not be changed. For example, if the thumbnail image 103 is divided as shown in FIG. 8A, when the divided area 125, which is a non-associated area, is selected, the division state of the main display area changes as shown in FIG. 9A. At that time, the division state of the thumbnail image 103 is maintained in the state shown in FIG. 8A. Subsequently, when the divided area 124 in FIG. 8A, which is an associated area, is selected, the main display area 102 returns to the division state shown in FIG. 4A. Then, the medical image data corresponding to the selected thumbnail image is displayed in the partial area 111 associated with the designated divided area 124. Note that the cases shown in FIGS. 9A to 9D are merely examples, and the present invention is not limited to these examples. The process in step S206 is similar to that in the first embodiment.

As described above, with the medical image display apparatus according to the second embodiment, in addition to the effects obtained in the first embodiment, the following effects are further obtained. That is to say, if a non-associated area in any thumbnail image is selected, display not depending on the division condition of the main display area can be realized. Accordingly, it is possible to provide a medical image display apparatus and a medical image display method that require less effort to display images in states intended by a user.

MODIFIED EXAMPLE 2-1

Figure 10A:
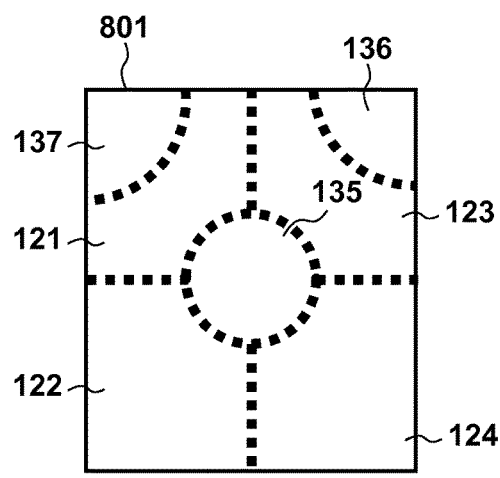
FIGS. 10A and 10B are diagrams showing division examples of a thumbnail image including a plurality of non-associated areas.
Figure 10B:
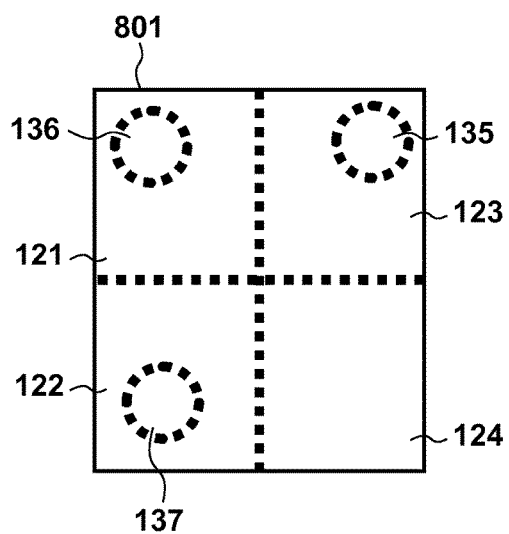

In the second embodiment, the case in which the number of non-associated areas in step S202 is one was described as an example. However, the number of non-associated areas may be plural. FIGS. 10A and 10B show division examples of the thumbnail image in a case where the number of non-associated areas is plural. FIGS. 10A and 10B show examples in which the thumbnail image 801 is divided into associated areas including the divided areas 121 to 124 and non-associated areas including divided areas 135 to 137. In this case, the same display method may be applied regardless of the non-associated area selected, but the display method applied in step S205 may be changed according to a non-associated area selected by the user in step S204. That is to say, a plurality of non-associated areas may be set in the thumbnail image, and different display methods may be respectively allocated to the non-associated areas. For example, when the divided area 135 in FIG. 10A, which is a non-associated area, is selected, the corresponding medical image data is displayed in full-screen, and, when the divided area 136, which is a non-associated area, is selected, the corresponding medical image data is MPR-displayed. Note that the division examples of the thumbnail image or the display method examples on the main display area when different non-associated areas are selected shown in FIGS. 10A and 10B are merely examples, and the present invention is not limited to these examples.

MODIFIED EXAMPLE 2-2

In the second embodiment, in step S202, thumbnail images having the same boundary lines are generated from all of the medical image data read in step S200. That is to say, all thumbnail images are divided in the same division condition. However, the division condition (arrangement state of the non-associated area) of the thumbnail image may be changed according to image information included in the medical image data corresponding to the thumbnail image.

For example, as shown in FIG. 14, correspondence between the image information obtained from the DICOM header or the like and the division condition is set in advance, and a thumbnail image is generated using the division condition corresponding to the image information contained in the medical image data. More specifically, if the image capturing modality of medical image data is a CT apparatus and the image capture site is a breast region, a thumbnail image having boundary lines as shown in FIG. 8A is generated. That is to say, referring to a table as shown in FIG. 14, it is determined that a non-associated area is located at the center and is in the shape of a circle. If the image capturing modality is an MRI apparatus and the image capture site is a head region, it is determined that a non-associated area is located at the upper right and is in the shape of a circle, referring to the table in FIG. 14, and, thus, a thumbnail image having boundary lines as shown in FIG. 8B is generated.

Furthermore, the division condition may be changed based on an image characteristic amount obtained when performing known image processing on the medical image data. For example, a smoothing filter is used on a thumbnail image before boundary lines overlaid thereon (corresponding image data), so that noise is removed. Then, binaryzation processing may be performed using a predetermined threshold (e.g., value 100) with respect to an image pixel value, so that an area inside the body and an area outside the body are separated from each other, and, based on that separate result, a non-associated area may be set. For example, a thumbnail image having boundary lines is generated such that a non-associated area is set in an area having a size that is at least a predetermined size, in the area outside the body. Note that the image information and the division conditions using the same described above are merely examples, and the present invention is not limited to these examples.

MODIFIED EXAMPLE 2-3

If a non-associated area is selected in step S204, then, in step S205, the display condition in the main display area may be changed according to the image information included in the medical image data corresponding to the selected thumbnail image. For example, as shown in the table in FIG. 15, correspondence between the image information obtained from the DICOM header or the like and the display condition in the main display area is set in advance, and display is performed in the main display area 102 in the display condition corresponding to the image information contained in the medical image data. More specifically, if the image capturing modality of medical image data is a CT apparatus and the image capture site is a breast region, it is determined that the display condition in the main display area is MPR display, referring to the table in FIG. 15, and, thus, the medical image data is displayed as in FIG. 9B in response to designation of the non-associated area. If the image capturing modality is an MRI apparatus and the image capture site is a head region, it is determined that the display condition in the main display area is time-course data display, referring to FIG. 15, and, thus, the medical image data is displayed as in FIG. 9C in response to designation of the non-associated area.

Furthermore, the display condition in the main display area may be changed taking, as the image information, an image characteristic amount obtained when performing known image processing on the medical image data. For example, known nodule detection processing may be performed on medical image data, and time-course data display may be performed if a nodule is detected, and MPR display may be performed if no nodule is detected. Note that the image information and the display conditions described above are merely examples, and the present invention is not limited to these examples.

Third Embodiment

Hereinafter, a medical image display apparatus according to the third embodiment will be described in which a thumbnail image is not divided, but directional information is given to the thumbnail image, so that a freely selected thumbnail image is displayed in a freely selected main display area.

Figure 11:
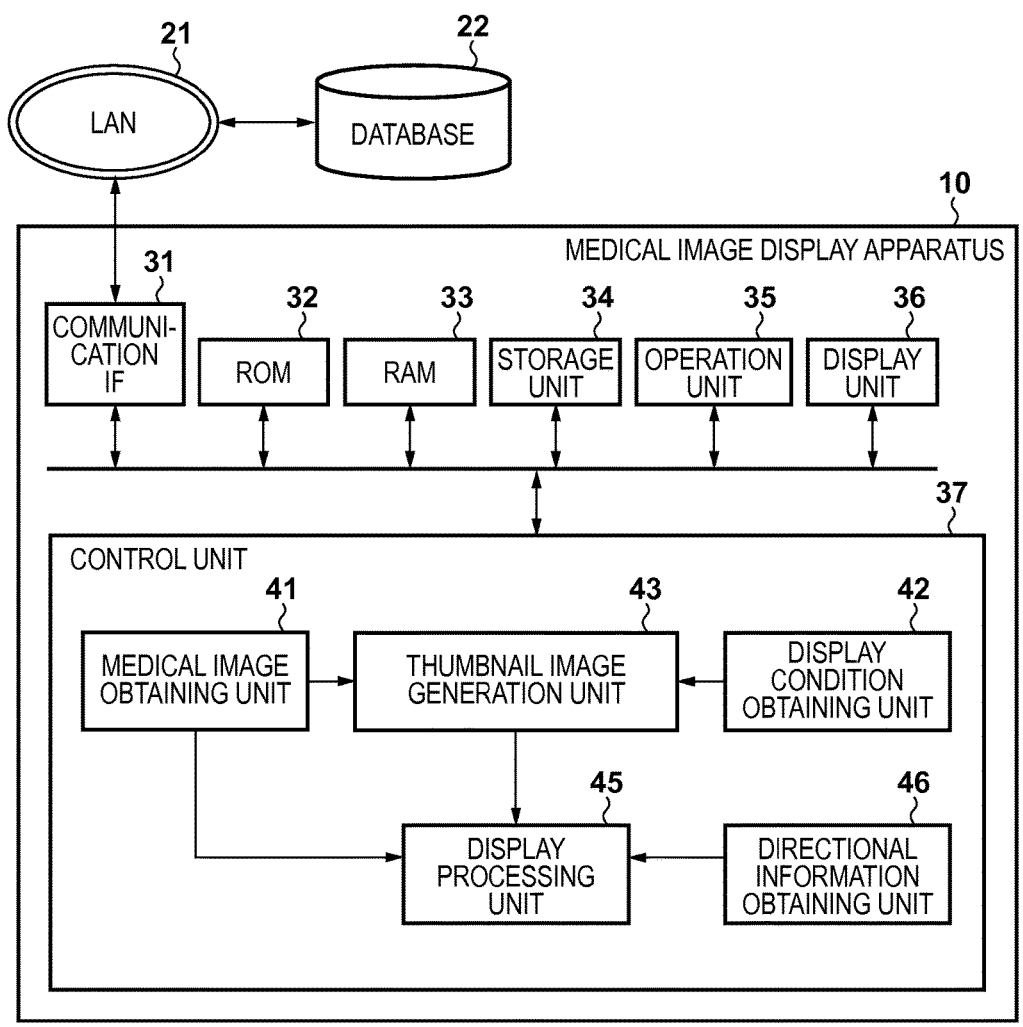
FIG. 11 is a block diagram showing a configuration example of a medical image display apparatus according to a third embodiment.

FIG. 11 shows a configuration example of the medical image display apparatus 10 according to the third embodiment. Comparison with the configuration example according to the first embodiment (FIG. 1) shows that the area information obtaining unit 44 has been omitted and a directional information obtaining unit 46 has been newly added. The directional information obtaining unit 46 accepts directional information input by the user via the operation unit 35 on a thumbnail image displayed on the display unit 36, and outputs it to the display processing unit 45. It is assumed that, as in the first embodiment, each functional unit of the control unit 37 is realized by software.

Figure 12:
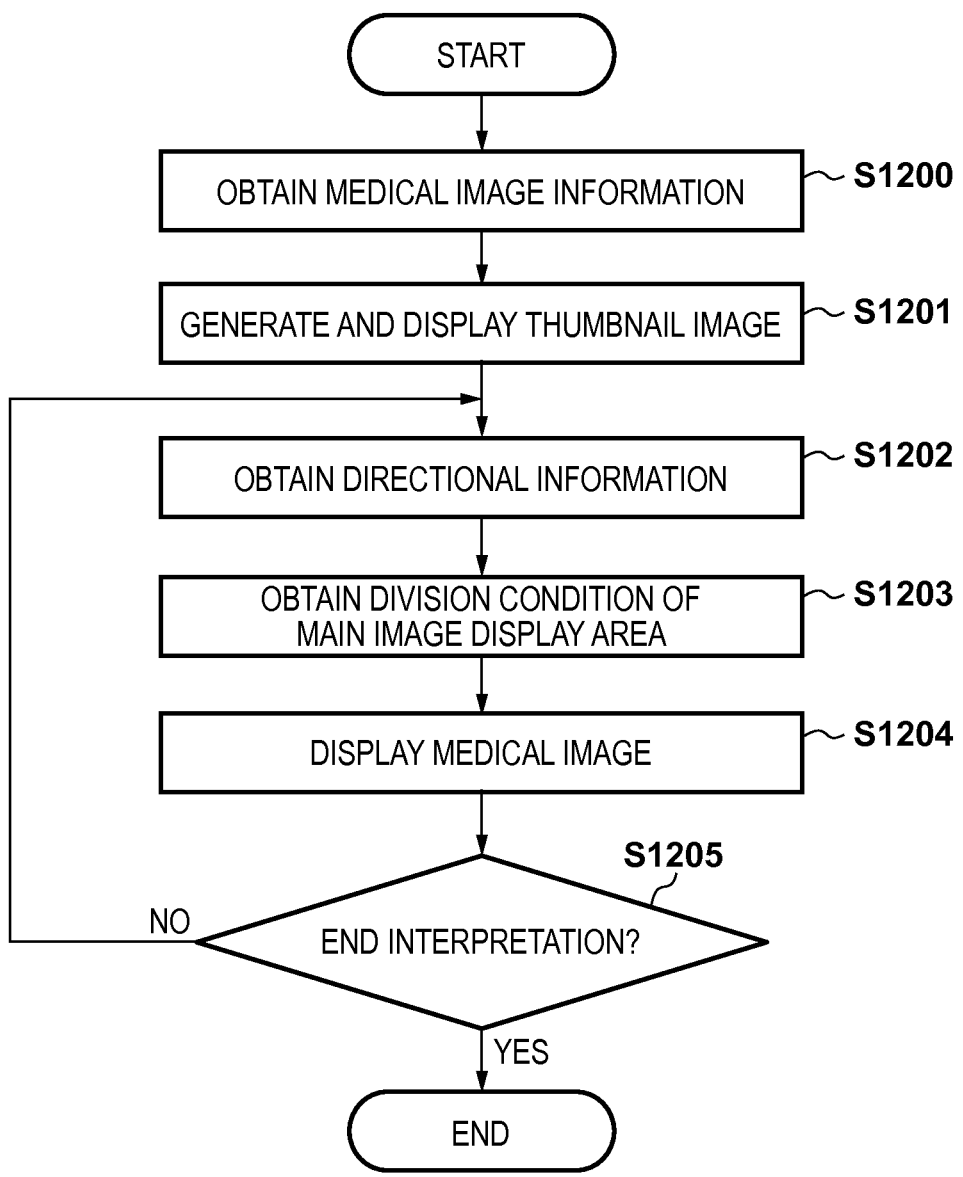
FIG. 12 is a flowchart illustrating the overall processing of the third embodiment.
Figure 13:
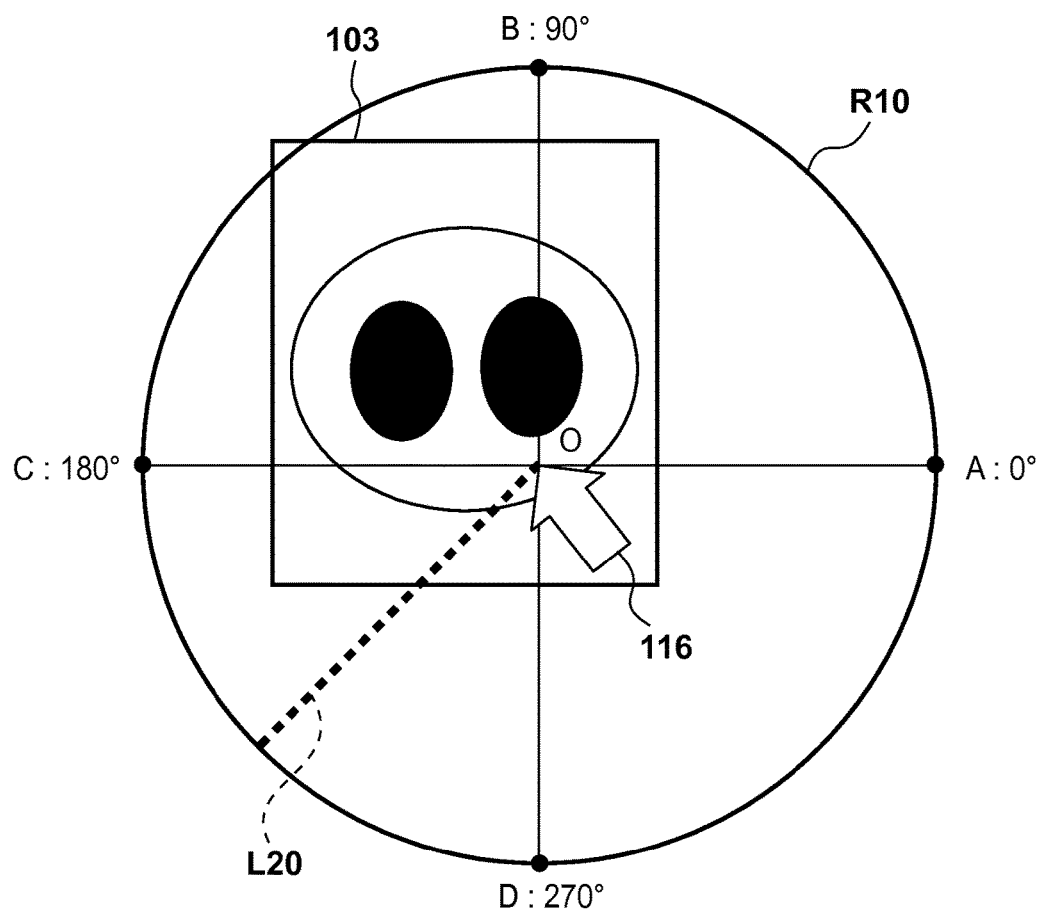
FIG. 13 is a diagram illustrating directional information according to the third embodiment.
Figure 16:
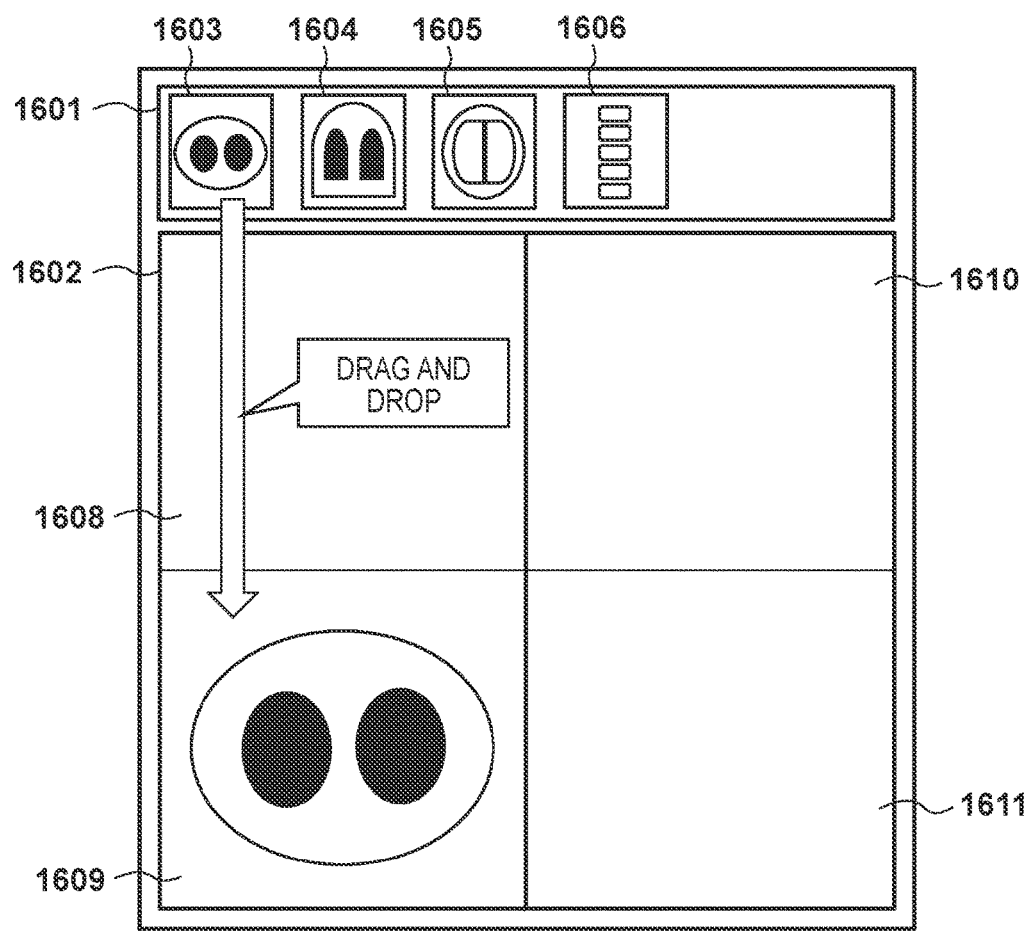
FIG. 16 is a diagram illustrating a drag-and-drop operation that displays medical image data.

Next, the overall processing by the control unit 37 in this embodiment will be described with reference to FIGS. 12 and 13. FIG. 12 is a flowchart of the processing performed by the control unit 37. FIG. 13 is a diagram illustrating a method in which the user inputs directional information on the thumbnail image 103 shown in FIGS. 3A and 3B. The arrow 116 indicates positional information (e.g., a mouse pointer) controlled by the operation unit 35. R10 denotes a circle in which the position indicated by the arrow 116 is taken as a center O. When the right direction of the arrow 116 is taken as 0°, points at which straight lines extending from the center O in directions of 0°, 90°, 180°, and 270° intersect the circle R10 can be respectively taken as A, B, C, and D.

The process in step S1200 is similar to that in step S200 in the first embodiment. The process in step S1201 is similar to that in step S202 in the first embodiment, but it is not necessary to generate boundary lines that are to be overlaid on the thumbnail image.

In step S1202, the user inputs directional information on a freely selected thumbnail image, via the operation unit 35. For example, the directional information is input using a mouse to select the thumbnail image 103 shown in FIG. 3A and drag it to a freely selected direction. Alternatively, if the display unit 36 is a touchscreen monitor, the directional information may be input on the thumbnail image 103, using an operation method commonly referred to as flick. For example, in FIG. 13, if the thumbnail image 103 is tapped (flicked) with a finger in the direction A, the directional information 0° is input. Furthermore, for example, if the thumbnail image is tapped (flicked) with a finger in a direction along the line segment L20 shown exactly at the middle between the line segment OC and the line segment OD, the directional information 225° is input.

The process in step S1203 is similar to that in step S201 in the first embodiment.

In step S1204, the medical image data corresponding to the thumbnail image on which the directional information is input in step S1202 is displayed in a partial area determined according to the directional information, among the partial areas in the main display area. For example, if the directional information input in step S1202 on the thumbnail image 103 in FIG. 3A is within a range of 0° to 90° shown in FIG. 13, the corresponding medical image data is displayed in the partial area 110 in FIG. 3A. In a similar manner, if the input directional information is within a range of 90° to 180°, the medical image data is displayed in the partial area 108, if the input directional information is within a range of 180° to 270°, the medical image data is displayed in the partial area 109, and, if the input directional information is within a range of 270° to 0°, the medical image data is displayed in the partial area 111. Furthermore, if an operation different from the operation that inputs the directional information on the thumbnail image is performed, the medical image data corresponding to the thumbnail image may be displayed in a display condition (e.g., FIGS. 9A to 9D) applied when a non-associated area is selected as shown in the second embodiment. The different operation is an operation such as pinch-in, pinch-out, or double-tapping on a touchscreen. These operations are merely examples, and other operation may be used.

The process in step S1205 is similar to that in step S206 in the first embodiment, and it is judged whether or not an instruction to end the interpretation has been received. If an instruction to end the interpretation has been received, the procedure in FIG. 12 is ended, and, if an instruction to end the interpretation has not been received, the procedure returns to step S1202.

As described above, with the medical image display apparatus according to the third embodiment, the following effects are obtained. That is to say, if directional information is input on a freely selected thumbnail image, medical image data corresponding to the thumbnail image can be displayed in the partial area in the main display area determined according to the directional information. Accordingly, it is possible to provide a medical image display apparatus and a medical image display method that require less effort to display medical image data in states intended by a user, without dividing a thumbnail image.

Note that the first to third embodiments described above and the modified examples shown in each embodiment can be used in a combination as appropriate.

As described above, according to the foregoing embodiments, it is possible to display freely selected medical image data as intended by a user with a small amount of effort.

Embodiments of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiments and/or that includes one or more circuits (e.g., application specific integrated circuit (ASIC)) for performing the functions of one or more of the above-described embodiments, and by a method performed by the computer of the system or apparatus by, for example, reading out and executing the computer executable instructions from the storage medium to perform the functions of one or more of the above-described embodiments and/or controlling the one or more circuits to perform the functions of one or more of the above-described embodiments. The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-120842, filed Jun. 11, 2014, which is hereby incorporated by reference herein in its entirety.

What is claimed is:

1. A medical image display apparatus for displaying a thumbnail image corresponding to medical image data, and displaying the medical image data in a display area upon selection of the thumbnail image, comprising:
   a determination unit configured to determine a display method of the medical image data in the display area, based on a divided area specified by a designated position in the thumbnail image when the thumbnail image is selected by a user, wherein the thumbnail image is divided into a plurality of divided areas; and
   a display control unit configured to display the medical image data in the display area, according to the display method determined by the determination unit,
   wherein the determination unit associates a plurality of partial areas obtained by dividing the display area and the plurality of divided areas, and
   determines the display method such that the medical image data is displayed in a partial area in the display area associated with a divided area to which the designated position belongs.

2. The apparatus according to claim 1,
   wherein the determination unit obtains a division condition indicating a manner for dividing the display area into the plurality of partial areas, and divides the thumbnail image into the plurality of divided areas according to the division condition.

3. The apparatus according to claim 2,
wherein a relative positional relationship between the plurality of partial areas is maintained in accordance with a relative positional relationship between the plurality of divided areas.

4. The apparatus according to claim 1,
wherein boundary lines between the divided areas are drawn on the thumbnail image.

5. The apparatus according to claim 1, further comprising:
a changing unit configured to change a display form such that a divided area to which the designated position in the thumbnail image belongs becomes identifiable with respect to the other divided areas before an instruction to select the thumbnail image.

6. The apparatus according to claim 5,
wherein the changing unit changes the display form according to whether or not medical image data has been already displayed in the partial area in the display area associated with the divided area to which the designated position belongs.

7. The apparatus according to claim 1, further comprising,
a changing unit configured to change a display form such that a partial area in the display area associated with a divided area to which the designated position in the thumbnail image belongs becomes identifiable with respect to the other partial areas before an instruction to select the thumbnail image.

8. The apparatus according to claim 1, further comprising:
a changing unit configured to change a display form such that a divided area associated with a partial area in which the medical image data displayed becomes identifiable with respect to the other divided areas.

9. The apparatus according to claims 1, further comprising:
a generation unit configured to, in a case where another medical image data has been already displayed in a partial area associated with a divided area to which the designated position belongs, generate new image data from both the medical image data corresponding to the thumbnail image to which the designated position belongs and the already displayed medical image data,
wherein the display control unit displays the new image data generated by the generation unit in the partial area associated with the divided area to which the designated position belongs.

10. A medical image display apparatus for displaying a thumbnail image corresponding to medical image data, and displaying the medical image data in a display area upon selection of the thumbnail image, comprising:
a determination unit configured to determine a display method of the medical image data in the display area, based on a divided area specified by a designated position in the thumbnail image when the thumbnail image is selected by a user, wherein the thumbnail image is divided into a plurality of divided areas; and
a display control unit configured to display the medical image data in the display area, according to the display method determined by the determination unit,
wherein the plurality of divided areas include both associated areas associated with a plurality of partial areas obtained by dividing the display area and a non-associated area associated with none of the plurality of partial areas, and
the determination unit is configured to determine,
in a case where a divided area to which the designated position belongs is one of the associated areas, the display method to be a first display method in which the medical image data is displayed in a partial area associated with the divided area, and
in a case where a divided area to which the designated position belongs is the non-associated area, the display method such that the medical image data is displayed according to a second display method, which is different from the first display method.

11. The apparatus according to claim 10,
wherein the second display method includes changing a division form of the display area.

12. The apparatus according to claim 10,
wherein a plurality of the non-associated areas are set in the thumbnail image, and
different display methods are respectively allocated to the non-associated areas.

13. The apparatus according to claim 10,
wherein an arrangement state of the non-associated area in the thumbnail image is determined based on image information included in medical image data to which the thumbnail image corresponds.

14. The apparatus according to claim 10,
wherein the display method corresponding to the non-associated area in the thumbnail image is determined based on image information included in medical image data to which the thumbnail image corresponds.

15. A medical image display apparatus for displaying a thumbnail image corresponding to medical image data, and displaying the medical image data in a display area upon selection of the thumbnail image, comprising:
an acceptance unit configured to accept an instruction to select the thumbnail image and input of directional information from a user, wherein the directional information is information with a reference position in the display area as a starting point;
a determination unit configured to determine a display position from a plurality of display positions in the display area, based on the directional information, wherein each of the plurality of display positions is associated with directional information; and
a display control unit configured to display the medical image data at the display position in the display area, which is determined by the determination unit.

16. The apparatus according to claim 15, wherein the determination unit determines the display position based on the reference position and a direction indicated by the directional information.

17. The apparatus according to claim 16, wherein the display position is located in the direction indicated by the directional information with the reference position.

18. The apparatus according to claim 15, wherein the reference position includes a center of the display area.

19. The apparatus according to claim 15, wherein the reference position is a center of the display area or periphery of the center.

20. The apparatus according to claim 15, wherein the direction information indicates a direction in which the user selects and drags the thumbnail.

21. A method for controlling a medical image display apparatus for displaying a thumbnail image corresponding to medical image data, and displaying the medical image data in a display area upon selection of the thumbnail image, comprising:
determining a display method of the medical image data in the display area, based on a divided area specified by a designated position in the thumbnail image when the thumbnail image is selected by a user, wherein the thumbnail image is divided into a plurality of divided areas; and displaying the medical image data in the display area, according to the determined display method, wherein the determining the display method associates a plurality of partial areas obtained by dividing the display area and the plurality of divided areas, and determines the display method such that the medical image data is displayed in a partial area in the display area associated with a divided area to which the designated position belongs.

22. A non-transitory computer-readable storage medium storing a program for causing a computer to execute the control method according to claim 21.

23. A method for controlling a medical image display apparatus for displaying a thumbnail image corresponding to medical image data, and displaying the medical image data in a display area upon selection of the thumbnail image, comprising:

accepting an instruction to select the thumbnail image and input of directional information from a user, wherein the directional information is information with a reference position in the display area as a starting point;

determining a display position from a plurality of display positions in the display area, based on the directional information, wherein each of the plurality of display positions is associated with directional information; and displaying the medical image data at the display position in the display area, which is determined in the determining.

24. A non-transitory computer-readable storage medium storing a program for causing a computer to execute the control method according to claim 23.

25. A medical image display apparatus for displaying a thumbnail image corresponding to medical image data, and displaying the medical image data in a display area upon selection of the thumbnail image, comprising:

at least one processor; and a memory having stored thereon instructions which, when executed by the at least one processor, cases the medical image display apparatus to:

determine a display method of the medical image data in the display area, based on a divided area specified by a designated position in the thumbnail image when the thumbnail image is selected by a user, wherein the thumbnail image is divided into a plurality of divided areas; and display the medical image data in the display area, according to the determined display method, wherein the determining associates a plurality of partial areas obtained by dividing the display area and the plurality of divided areas, and determines the display method such that the medical image data is displayed in a partial area in the display area associated with a divided area to which the designated position belongs.

26. A medical image display apparatus for displaying a thumbnail image corresponding to medical image data, and displaying the medical image data in a display area upon selection of the thumbnail image, comprising:

at least one processor; and a memory having stored thereon instructions which, when executed by the at least one processor, cases the medical image display apparatus to:

accept an instruction to select the thumbnail image and input of directional information from a user, wherein the directional information is information with a reference position in the display area as a starting point;

determine a display position from a plurality of display positions in the display area, based on the directional information, wherein each of the plurality of display positions is associated with directional information; and display the medical image data at the determined display position in the display area.

27. A medical image display apparatus for displaying a thumbnail image corresponding to medical image data, and displaying the medical image data in a display area upon selection of the thumbnail image, comprising:

a determination unit configured to determine a display position of the medical image data in the display area, based on a designated position in the thumbnail image when the thumbnail image is selected by a user; and a display control unit configured to display the medical image data in the display area, according to the display position determined by the determination unit, wherein a plurality of partial areas obtained by dividing the display area is associated with a plurality of divided areas, and the determination unit determines the display position such that the medical image data is displayed in a partial area in the display area associated with a divided area to which the designated position belongs.

28. A medical image display apparatus for displaying a thumbnail image corresponding to medical image data, and displaying the medical image data in a display area upon selection of the thumbnail image, comprising:

an acceptance unit configured to accept an instruction to select the thumbnail image and an instruction to input directional information from a user, wherein the directional information is information with a reference position in the display area as a starting point;

a determination unit configured to determine a display position from a plurality of display positions in the display area, based on the directional information, wherein each of the plurality of display positions is associated with directional information; and a display control unit configured to display the medical image data at the display position in the display area, which is determined by the determination unit.

29. The apparatus according to claim 28, wherein the instruction to input directional information from a user is input by a flick operation.

30. The apparatus according to claim 28, wherein the display area includes a thumbnail image display area.

31. The apparatus according to claim 28, wherein the reference position is different from a position designated by a user at the time of selecting the thumbnail image.

32. A method for controlling a medical image display apparatus for displaying a thumbnail image corresponding to medical image data, and displaying the medical image data in a display area upon selection of the thumbnail image, the method comprising:

determining a display method of the medical image data in the display area, based on a divided area specified by a designated position in the thumbnail image when the thumbnail image is selected by a user, wherein the thumbnail image is divided into a plurality of divided areas; and controlling to display the medical image data in the display area, according to the display method determined by the determination unit, wherein the plurality of divided areas include both associated areas associated with a plurality of partial areas obtained by dividing the display area and a non-associated area associated with none of the plurality of partial areas, and in the determining the display method, in a case where a divided area to which the designated position belongs is one of the associated areas, the display method is determined to be a first display method in which the medical image data is displayed in a partial area associated with the divided area, and in a case where a divided area to which the designated position belongs is the non-associated area, the display method is determined such that the medical image data is displayed according to a second display method, which is different from the first display method.

33. A non-transitory computer-readable storage medium storing a program for causing a computer to execute the control method according to claim 32.

34. A medical image display apparatus for displaying a thumbnail image corresponding to medical image data, and displaying the medical image data in a display area upon selection of the thumbnail image, comprising:

at least one processor; and a memory having stored thereon instructions which, when executed by the at least one processor, cases the medical image display apparatus to:

determine a display method of the medical image data in the display area, based on a divided area specified by a designated position in the thumbnail image when the thumbnail image is selected by a user, wherein the thumbnail image is divided into a plurality of divided areas; and control to display the medical image data in the display area, according to the display method determined by the determination unit, wherein the plurality of divided areas include both associated areas associated with a plurality of partial areas obtained by dividing the display area and a non-associated area associated with none of the plurality of partial areas, and in the determining the display method, in a case where a divided area to which the designated position belongs is one of the associated areas, the display method is determined to be a first display method in which the medical image data is displayed in a partial area associated with the divided area, and in a case where a divided area to which the designated position belongs is the non-associated area, the display method is determined such that the medical image data is displayed according to a second display method, which is different from the first display method.

* * * * *